(12) United States Patent
Caruso

(10) Patent No.: US 10,268,052 B2
(45) Date of Patent: Apr. 23, 2019

(54) DEVICE AND METHOD FOR PROTECTING THE EYES FROM RADIATION

(71) Applicant: Giuseppe Nunzio Caruso, Neuhausen (CH)

(72) Inventor: Giuseppe Nunzio Caruso, Neuhausen (CH)

(\*) Notice: Subject to any disclaimer, the term of this patent is extended or adjusted under 35 U.S.C. 154(b) by 206 days.

(21) Appl. No.: 15/322,470

(22) PCT Filed: Jul. 13, 2015

(86) PCT No.: PCT/EP2015/065958
§ 371 (c)(1),
(2) Date: Mar. 15, 2017

(87) PCT Pub. No.: WO2016/008839
PCT Pub. Date: Jan. 21, 2016

(65) Prior Publication Data
US 2017/0199397 A1 Jul. 13, 2017

(30) Foreign Application Priority Data
Jul. 13, 2014 (EP) .................... 14176838.2

(51) Int. Cl.
*G02C 7/10* (2006.01)
*G02B 26/02* (2006.01)
(Continued)

(52) U.S. Cl.
CPC .............. *G02C 7/104* (2013.01); *A61F 9/023* (2013.01); *A61F 9/045* (2013.01); *G02B 26/02* (2013.01); *G02C 7/101* (2013.01); *G02C 7/16* (2013.01)

(58) Field of Classification Search
CPC .......... G02C 7/10; G02C 7/101; G02C 7/104; G02C 7/16; G02B 26/02; G02B 26/023; A61F 9/022; A61F 9/023
(Continued)

(56) References Cited

U.S. PATENT DOCUMENTS 4,848,890 A * 7/1989 Horn ................... A61F 9/023
351/44
5,276,539 A * 1/1994 Humphrey ............ A61B 3/063
349/116

(Continued)

*Primary Examiner* — Darryl J Collins

(57) ABSTRACT

Device (1) for protecting eyes from radiation, preferably from 100 nm to 1 mm and in particular from UV light or infrared, comprising at least two sensor arrangements (2/3), external (2) and internal sensor arrangement (3), wherein each sensor arrangement (2/3) comprises plurality of radiation sensors (2a/3a) arranged one after the other, which are each arranged along closed curve (2b/3b), and wherein the internal sensor arrangement (3) is surrounded by the external (2), and wherein the external and internal sensor arrangement (2/3) are arranged adjacently to each other, and wherein the internal sensor arrangement (3) encloses radiation passage region (4), and wherein the radiation passage region (4) comprises radiation passage opening (5), and wherein a closing device (6) is arranged in such a way with respect to the radiation passage region (4) that an incident radiation (S) passing through the radiation passage opening (5) is either let pass through or at least partially attenuated, and comprising control device (8) which is connected to the internal sensor (2), the external sensor arrangement (3) and the closing device (6).

15 Claims, 4 Drawing Sheets

(51) Int. Cl.
*A61F 9/02* (2006.01)
*A61F 9/04* (2006.01)
*G02C 7/16* (2006.01)

(58) Field of Classification Search
USPC ...... 351/44, 45, 47; 359/227, 350, 361, 601, 359/614; 250/472.1, 473.1, 474.1, 515.1, 250/516.1
See application file for complete search history.

(56) References Cited

U.S. PATENT DOCUMENTS

| | | | | |
|---|---|---|---|---|
| 5,841,507 A | * | 11/1998 | Barnes | G02C 7/101 351/49 |
| 2012/0204303 A1 | * | 8/2012 | Seo | A61F 9/023 2/12 |
| 2015/0323795 A1 | * | 11/2015 | Alton | G02B 27/0172 349/11 |

* cited by examiner

DEVICE AND METHOD FOR PROTECTING THE EYES FROM RADIATION

The invention relates to a device for protecting the eyes against radiation. The invention further relates to a method for the protection of the eyes against radiation.

STATE OF THE ART

More and more attacks against persons are taking place, in which laser, strong light or infrared radiation are being used. Therefore there is a need to protect the eyes of such people, for example, pilots, bus drivers, train drivers, police guards or military against such radiation, for instance, to avoid damage or accidents.

Devices that protect the eyes from radiation attacks are known, for example from the documents U.S. Pat. No. 5,828,437 or 5,255,117. Such devices have the disadvantage that the eye is protected insufficiently.

BRIEF DESCRIPTION OF THE INVENTION

The task of the invention is a device and a method in order to protect the eyes of persons.

This object is achieved with a device having the features set forth in claim 1. The dependent claims 2 to 10 relate to further advantageous embodiments. The object is further achieved by a method having the features set forth in claims 5 11. The dependent claims 12 to 15 relate to further advantageous method steps.

The object is in particular achieved by a device to protect the eyes from radiation, preferably in the range of 100 nm up to 1 mm, and especially against UV, light, or IR, comprising of at least two sensor arrangements, an external sensor arrangement and an inner sensor arrangement, wherein each sensor arrangement comprises a plurality of radiation sensors arranged one after the other, which are each arranged along a closed curve, and wherein the internal sensor arrangement is surrounded by the external sensor arrangement, and wherein the external and internal sensor arrangement are arranged adjacently to each other, and wherein the internal sensor arrangement encloses a radiation passage region, and herein the radiation passage region comprises a radiation passage opening, and wherein a closing device is arranged in such a way with respect to the radiation passage region, that an incident radiation passing through the radiation passage opening is either let pass through or completely closed or at least partially attenuated by a tinted surface, and comprising a control device which is connected to the internal sensor arrangement, the external sensor arrangement and the closing device.

The object is further achieved by a method for protecting the eyes from radiation, preferably in the range of 100 nm to 1 mm, and more particularly against UV light, or IR, wherein the eye is surrounded by at least two sensor arrangements, an external sensor arrangement as well as an internal sensor arrangement, wherein each sensor arrangement comprises a plurality of radiation sensors arranged one after another along a closed curve and wherein the internal sensor arrangement is surrounded by the external sensor arrangement, and wherein the internal sensor arrangement surrounds a radiation passage region, and wherein a radiation passage opening is arranged in the radiation passage region, and wherein a closing device is arranged in such a way with respect to the radiation passage region that an incident radiation is either let pass through or at least partially attenuated, whereby the closing device is closed if the external sensor arrangement and subsequently the internal sensor arrangement is irradiated by the incident radiation, or only the second sensor arrangement is irradiated and the closing device is opened again, if first the internal sensor arrangement and subsequently only the external sensor arrangement is irradiated by the incident radiation and both sensor arrangements are irradiated together, then the closing device will be closed as soon as the programmed values would be exceeded.

The term "light" is used herein as visible light in a waveband from 380 nm to 780 nm.

Radiation attacks are often carried out with lasers. For example, pilots can be blinded by laser attacks. Laser beams have, depending on the distance of the attack, a different point size or a different beam diameter. In 10000 m distance the point size can be approximately 10 m, in 2500 m approx. 2.5 m, in 1250 m approximately 1.25 m. In closer distances like 50 m approx. 0.05 m and in 25 m 0.025 m and in a distance of only 10 m only 0.01 m.

The inventive device has the advantage that even a small point size or a small beam diameter can be safely blocked because the device recognizes the approach of the beam and the closing device interrupts the beam as soon as this hits the external sensor arrangement and subsequently the internal sensor arrangement, so that the beam no longer gets directly onto the eye. Once the beam has returned from on the internal sensor arrangement to the external sensor arrangement, and the internal sensor arrangement is not illuminated anymore, the closing device may reopen. In practice this means that the closing device is closed only for a very short time, so that the eye of the pilot is covered only for a very short time and the pilot has clear view most of the time and does not get distracted. A mechanical closing device or also an electronic closing device are hereby preferably used, as these are known for example from cameras with shutter speeds in the range from $10^{-3}$ to $10^{-18}$ seconds preferably. The shutter speeds can therefore be very short, for example in the range of milliseconds to atto-seconds. One blink lasts about 0.25 s. The eye is thus too slow to effectively protect against laser attacks. Shutter speed is defined as the time duration to bring the closing device from the open state to the closed state. The fast shutter speed of the inventive device thus has the advantage that the eye of the pilot or the affected person can be better protected because the eyelid closes only in about 0.25 sec., especially in laser attacks that are performed with a short and or further distance and have a higher performance.

Basically, the stronger the laser radiation, the faster the shutter should be closed in order to protect the eye from an excessive radiation exposure since the threshold values are getting shorter if measured by radiation intensity (m/w) in time. The inventive device has the particularly advantageous property that the closure or the closing device is preferably opened immediately again, and this preferably even individually, so that right and left sides work autonomously once the laser beam is no longer within the radiation passage region is, so that the pilot, train driver, bus driver, etc. regains visibility very quickly on the attacked eye. In an advantageous embodiment the opening time, that means the length of time to bring the closing device from the closed to the open state, should also be in the range of $10^{-3}$ to $10^{-18}$ seconds, preferably. Thus, the closing device remains preferably closed as long the laser beam is not within the radiation passage region anymore, in order to be reopened instantly afterwards. Advantageously, the closing device remains closed, depending on the duration of irradiation, while the radiation passage region is irradiated by the laser beam, wherein the irradiation time can be, depending on the situation, in the range of fractions of seconds, in unfavorable cases however also with a longer exposure time, for example in the range of several seconds.

In a particularly advantageous embodiment a separate closing device is arranged in front of the left and the right eye, whereby the two closures are working independently. In a laser attack with small beam sizes it is thus possible that only either the left or the right eye is attacked simultaneously, with the result that usually at least one eye has clear view.

The inventive apparatus comprises in a particularly advantageous embodiment and has the advantage that the direction of movement of a radiation attack can be detected because the device comprises two juxtaposed sensor arrangements, whereby each sensor arrangement comprises a plurality of individually measurable sensors. Based on these measured values it is possible, using an evaluation device, to calculate the radiant intensity.

In a further advantageous embodiment the measured direction of incidence is stored in the inventive device, preferably together with other data such as the time, the radiation intensity or the place, coordinates, for example based on GPS data or the height, for example could be recorded with MEMS sensors (CRG20, SiRRS01, PinPoint, Gemini) and electronics and via communications telephone, SMS, etc. could be passed on.

Based on this information, it is preferably instantaneous or subsequently possible to determine the emission point of the laser attack at least approximately.

In the inventive device preferably a mechanical or electronic closing device is advantageously used, as this is known for example in cameras. Such closing devices are also called shutters. Such a closing device usually measures a radiation transmission of 100% or smaller in an open state, i.e. the beam entering through the closing device has no or only a slight damping effect.

The inventive device is therefore particularly advantageous for pilots, because the standards ISO 12311-1, ISO 12312-1 or EN166 stipulate that a light transmittance of 75% is required.

The inventive device therefore also has the advantage that a good color recognition is guaranteed and no color deterioration takes place, since no wavelengths are filtered out. Thus, the inventive device fulfills the standards ISO 12312-1, ISO 123111, EN 166 regarding color recognition in aviation, shipping, railways and in land transport, particularly from modern color digital or analog displays.

A mechanical closing device also has the advantage that it can easily break radiation into a big wavebands. In the inventive device, for example, sensors with a sensitivity wavelength range of 400 nm to 1100 nm will be used.

Polarizing filters or laser goggles are known as examples for protection against laser attacks. The disadvantage of polarization filters the fact that these are not allowed in aviation since the onboard instruments are no longer recognizable. The disadvantage of laser safety eyewear is the fact that there are lasers comprising a plurality of different wavelengths. Laser safety goggles can only filter the permanently fixed and predetermined wavelengths, so that there is the risk that laser safety goggles do not filter the all the irradiating laser.

The inventive device has the further advantage that laser attacks with high radiation strength can be entirely blocked since the optical beam path is interrupted by a mechanical closing device.

Known devices will let some residual radiation pass through with certain radiation intensity, so that a complete protection cannot be ensured. For example, a point beam can penetrate an LCD and it also depends in which angle the radiation hits the LCD, the beam can be stronger or weaker. In the preferred embodiment of the present invention, the radiation passage opening is closed completely with help of the closing device. Thus, it is not possible, that with stronger lasers, the residual light can cause damage anyway.

The inventive device will have also in a further advantageous embodiment, at least one camera and a display, wherein the display is arranged in the interior of the spectacles and the camera on the exterior of the glasses so that the camera records data in 2D or 3D, or records an external image in SWIR, MWIR, LWIR, and reproduces it on the display, so that a pilot can be presented with his environment as detailed as possible, even if both closing devices are temporarily closed for a short time. If an interface of the computer exists, it is also possible to display additional data such as flight data directly onto the screen.

The inventive measuring device may in a further advantageous embodiment, also include a filter which is arranged in front of the spectacles, and would filter the incoming radiation, such as UVC, UVB, UVA and blue light as well as infrared.

The invention is described in detail below with reference to all embodiments.

BRIEF DESCRIPTION OF DRAWINGS

The drawings used to explain the embodiments show.

In general, the same parts have the same reference signs in the drawings.

WAYS OF CARRYING OUT OF THE INVENTION

Figure 1:
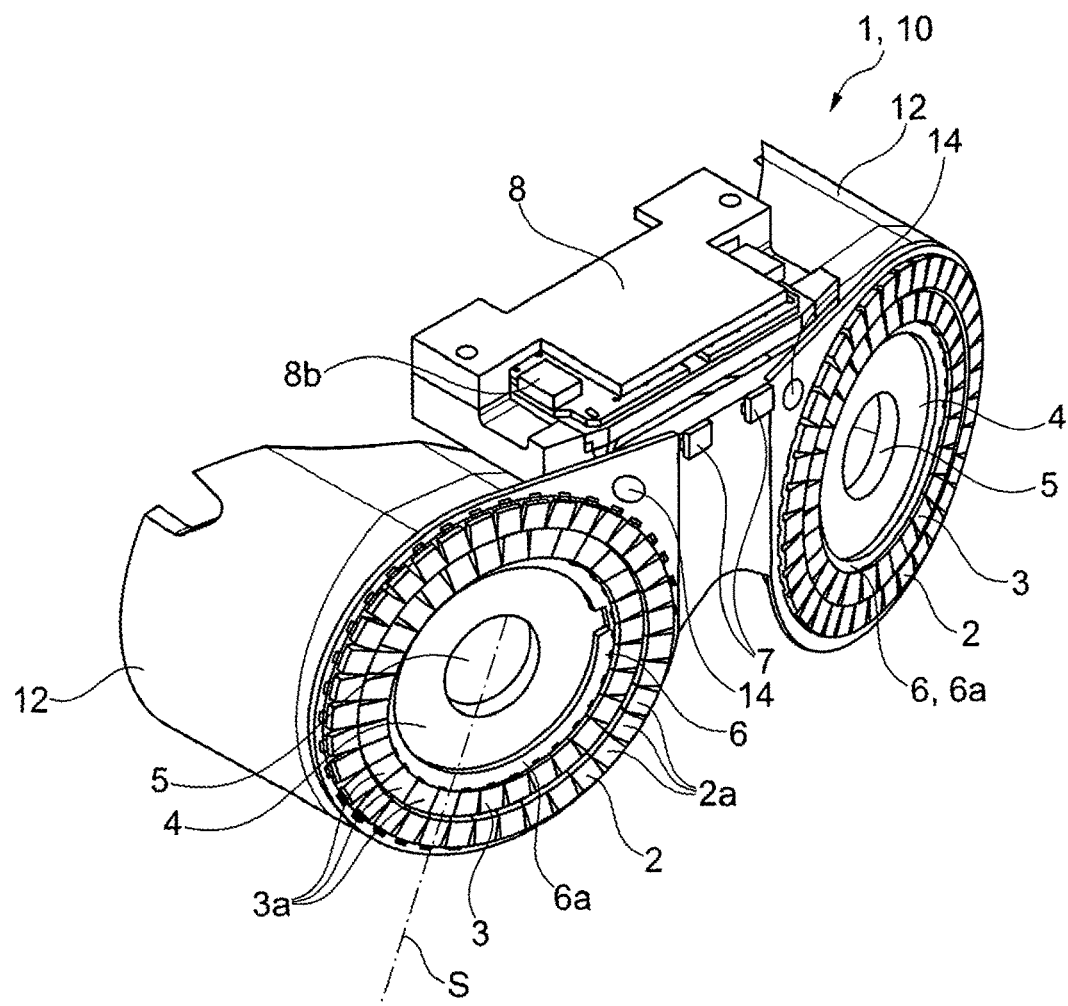
FIG. 1 a perspective view of a device designed as a spectacle attachment.

The device for protection against laser attacks, increased radiation or stronger light, that is based on a sophisticated UV, light and IR sensor system and that passes the impulse in micro-, nano-, pico-, femto-, atto-, zepto up to yocto-seconds to the closing device and that can open and close at least one or more closing devices in micro-, nano-, or up to atto or faster. This laser and strong light protection shall protect the eye from dangerous and intense radiation that exceed the thresholds, better and faster because one blink lasts 0.25 sec and thus is too slow in this energy range. It is important that the protection device works in close-less than one meter, and in long range.

Today's laser goggles cover only certain wavelengths. The frequencies of laser devices which are however available on the market, starting with the UV radiation from 157 nm, 193 nm, 213 nm, 222 nm, 224.3 nm, 248 nm, 266 nm, excimer XeCl 308 nm, 325 nm He—Cd, 332.4 nm, 347 nm, 351 nm, 355 nm 20 and then continuing with the visible light where laser with the following wavelengths such as 402 nm, 432 nm, 441.6 nm, 488 nm, 510.5 nm, green laser with 532 nm, 539.5 nm, 543.5 nm, yellow 578.2 nm, 594.1 nm, up to the red laser with 611.9 nm, 632.8 nm, 647.1 nm, 694 nm and then it continues with the infrared range as Nd. Yag 946 nm, 25 Nd. Yag 1064, 1047 nm, 1079 nm, 1152 nm, 1315 nm, 1319 nm, 1523 nm, 1540 nm, 2001 nm, 2008 nm, 2079 nm, 2090 nm, 3391 nm up in distance IR 1 mm.

The twilight and night area therefore requires at least a light transmission of more than 75%. (see standardization ISO 12312-1 or EN 166.) Developments or laser protection that work with LCD, OLED and other technologies can also not be used in the twilight and in the night area. Reason for this is again that the light transmittance must be above 75%. The LCD technology works with polarizing filter, as the light transmittance is below the 75% at approx. 40%-50%.

This intense light can temporarily distract pilots and drivers. The visibility of the affected persons can be temporarily affected, disturbed or blocked. Critical phases of flights are:

Start, approach, landing and emergency maneuvers. If the glasses block for a fraction of less than one second, then the person can engage on the incident and act. Otherwise, he has no vision for a short or long period since the eye was overloaded with the radiation. Other concerns are potential eye injuries, which affect the entire eye, including the cornea, conjunctiva, iris, lens, vitreous, macula and retina. Moreover, in the evening or at night, there is a difference of the dark environment with strong light which is very high, so that the eye is affected even more by the extreme situation. (More information about laser protection can be found 20 under the BGI 5092 and can be read there).

On top of that the laser beams have a different point size (beam diameter) depending on the distance. In 10000 m the point size is approx. 10 m, at 2500 m approx. 2.5 m, in 1250 m approx. 1.25 m. With closer distances like 50 m approx 0.05 m and in 25 m 0.025 m and at a distance of 10 m only 0.01 m. Thus there is a danger in close distance areas, such as the police, tram, bus drivers, train drivers, motorists, etc., where the distance is below 50 m and less than 10 m as compared to flying. Whereas helicopter pilots can also experience this close range. The closer the laser beam, the more intense the energy. Thus the eye must be protected in all situations, close and far.

Also glasses with anti-reflective coating have a light transmission of less than 60% and thus do not reach the 75% light transmittance. These are the international guidelines of ISO 123121 and ISO 12311.1 or EN 166.

If one is omitting the individual colors as some manufacturers do to stop the specific wavelength, then a color discrimination takes place instead and thus the safety in aviation or in the transport and shipping area is at risk.

Laser safety eyewear are subject to the European Guidelines for Personal Protective Equipment (PPE Directive 89/686/EEC). They are not approved for road traffic.

According to DIN EN 207 the protection must withstand at least 10 s.

For example, a higher protection against acids, alkalis or toxic or reactive gases and vapors. The sensors can be protected against dirt and are coated depending on application with the corresponding transparent or tinted material such as quartz, polymers such as polycarbonate, polyester, copolyester, cellulose propionate, acetate or other polymers.

The construction of the laser protection may not only exist from the front but also all around the eye it must be protected. The radiation may not enter laterally, nor from above or below. It is also crucial to maintain a very large view area, so that security is not limited.

Therefore, one should at least guarantee to have 90° to 180° or more viewing area.

The skin is generally less sensitive against laser beams than the eye. The effect of laser beams to the skin is highly dependent on the intensity of the radiation and it would not only damage the top layer of skin, but also the lower skin layer can be affected by the high intensity. Laser radiation with a high intensity can lead to burns, severe blistering and subsequent scarring of the skin.

| European class | American class | Typical performance in milliwatts (mW) | Examples of applications |
|---|---|---|---|
| Classification 1 | Classification I | <0.4 mW | DVD players |
| Classification 2 | Classification II | <1 mW | Laser pointer |
| Classification 3R | Classification IIIa | <5 mW | Showlaser |
| Classification 3b | Classification IIIb | <500 mW | Showlaser, medical/cosmetic lasers |
| Classification 4 | Classification IV | >500 mW | Showlaser, medical/cosmetic lasers |

Further information can be found in the literature on the thresholds which are represented in mW and also in time units. These values can be adjusted via software.

FIG. 1 shows a device 1 designed as spectacle attachment to protect eyes from radiation, preferably in the range from 100 nm to 1 mm and in particular from UV, light, or IR. The device 1 comprises of at least two sensor arrangements 2,3, an external sensor arrangement 2 as well as an internal sensor arrangement 3, wherein each sensor arrangement 2,3 has a plurality of sequentially followed arranged radiation sensors 2a, 3a which are each arranged on a closed curve path 2b, 3b. The curve path can run in a variety of possible forms, advantageously circular or oval, but also, for example as polygonal, for example triangular or quadrangular. The internal sensor arrangement 3 is enclosed by the external sensor arrangement 2, wherein the external and the internal sensor arrangements 2,3 are arranged horizontally to each other, and wherein the internal sensor arrangement 3 encloses a radiation passage region 4.

Figure 5:
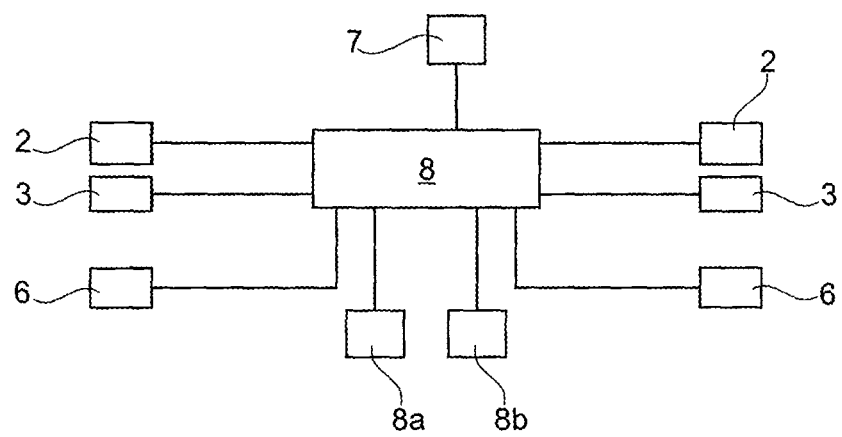
FIG. 5 a schematic signal diagram for a control device.

The radiation passage region 4 has a radiation passage opening 5. A mechanical closing device 6 is arranged relative to the radiation passage region 4, in a way that an incident radiation S can either pass through the radiation passage opening 5 or is at least partially attenuated. An electronic control device 8, as illustrated in FIG. 5 is signal conductively connected to the internal sensor arrangement 2, the external sensor arrangement 3 and the closing device 6.

The closing device 6 comprises of at least one mechanically movable element 6a, which lets the incident radiation S either pass through or at least partially attenuates.

Advantageously the movable element 6a allows the incident radiation S to either fully pass or stops it completely. The closing device 6 preferably has a shutter speed in the range from 10-3 to 10-18 seconds.

The mechanically movable element 6a is preferably radiopaque or configured of different OD (Optical Density) and can have a mirrored surface.

The mechanically movable element 6a can have a radiation transmission in the range of 5% up to 99% in an advantageous embodiment.

Figure 2:
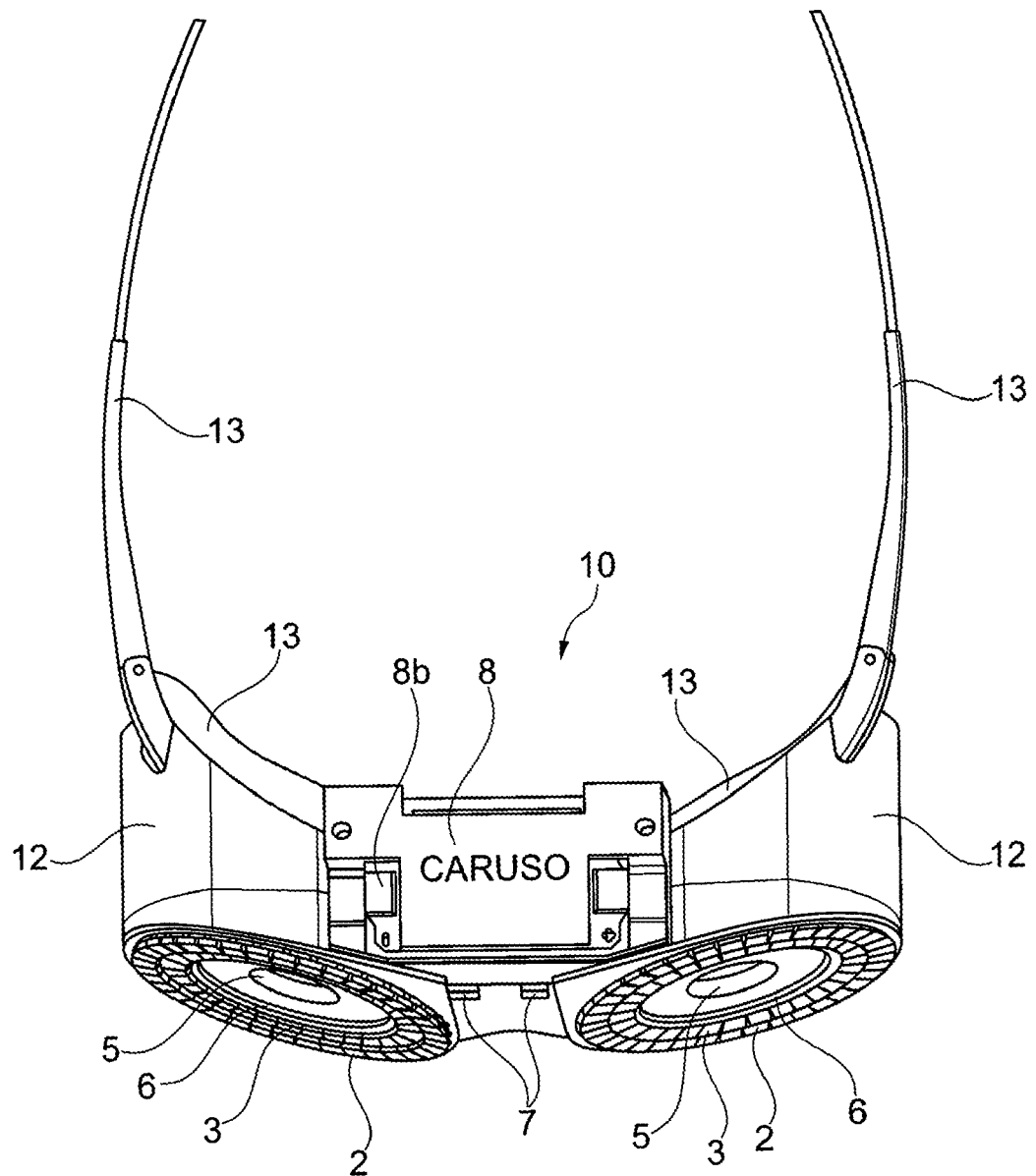
FIG. 2 a plan view of a pair of glasses with spectacle attachment.

The device 1 can be designed, as shown in FIG. 1, as spectacles 10 or, as shown in FIG. 2, as spectacle attachment 10 on glasses 13. The glasses 13 may include corrective lenses. The glasses 13 may further comprise of a protective filter, so that it is colored and has a light transmittance in the range from 100% to 0%. In this area the device 1 advantageously has a surrounding cover 12 which prevents a lateral non-occurrence.

FIGS. 1 and 2 show a device 1 for glasses or spectacles, with two reciprocal spaced-apart radiation passage regions 4, each with a radiation passage opening 5 and each with one closing device 6, wherein each radiation passage region 4 is surrounded by an internal and an external sensor arrangement 2,3. The two closing devices 6 are advantageously controlled individually.

The device 1 shown in FIGS. 1 and 2 includes advantageously an ambient radiation sensor 7 for detecting the ambient radiation.

The device 1 could additionally also include a non-illustrated soluble optical filter, which is connectable with the device in a way, that the optical filter is arranged in front of the sensor arrangement to 2,3, the radiation passage regions 4 and preferably also the ambient radiation sensor 7, in order to filter incident radiation to protect, in particular, the ambient radiation sensor 7 of an excessive light intensity.

The device 1 has, as shown in FIG. 5, has a control device 8 and preferably a memory device 8*a* as well as a data interface 8*b*. The control device 8 is connected signal-conducting with the external sensor arrangement 2 of the internal sensor arrangement 3 and the closure device 6.

Figure 3:
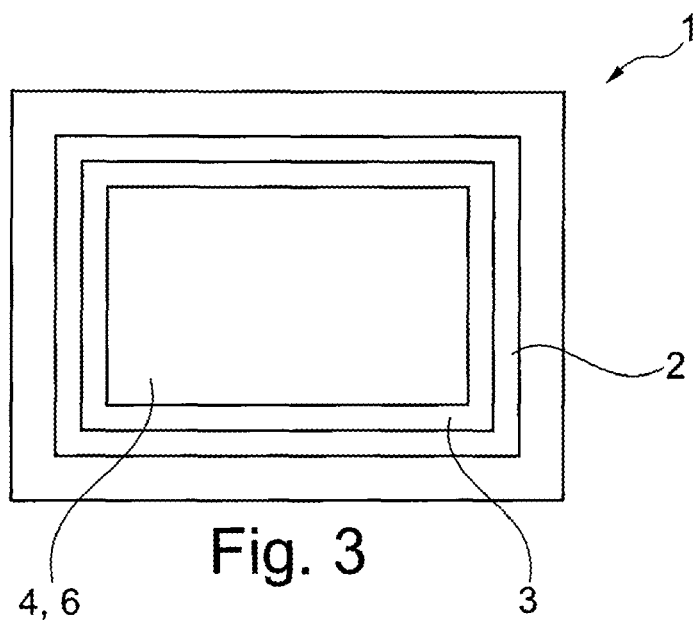
FIG. 3 a schematic view of a device with a closing device using LCDs or other technologies which allow a blackout.

FIG. 3 shows an embodiment of a device 1 with external and internal sensor arrangement 2,3, radiation passage region 4 and radiation passage opening 5. The radiation passage opening 5 is at the same time the closing device 6, which is configured as electronic-optical radiation shutter, for example, as LCD radiation shutter.

The device is operated in such a way that an incident radiation S is either let pass through or at least partially attenuated through the radiation passage opening 4, whereby the closing device 6 is closed if the external sensor arrangement 2 and subsequently the internal sensor arrangement 3 is irradiated by the incident radiation S and wherein the closure device 6 is opened again when first the internal sensor arrangement 3 and subsequently only the external sensor arrangement 2 is irradiated by the incident radiation S. FIGS. 4*a* to 4*e* show such a method. The figures show an external sensor arrangement 2 and an internal sensor arrangement 3.

Figure 4A:
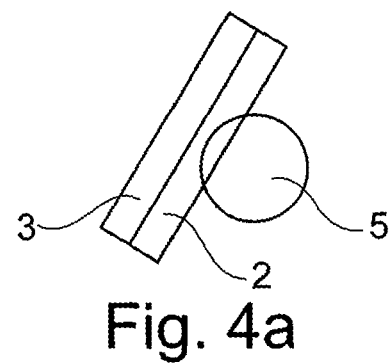
FIG. 4a-4e an exemplary procedure for closing and opening of the device.
Figure 4B:
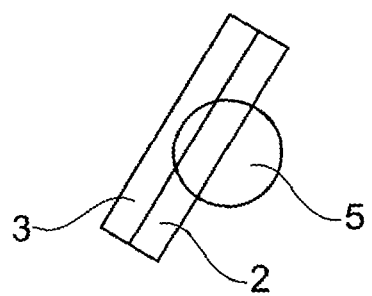

In FIG. 4*a*, the incident radiation S approaches the external sensor arrangement 2 and irradiates it. In FIG. 4*b*, the incident radiation S is more advanced and also irradiates the internal sensor arrangement 3. Once the control device 8 recognizes this condition, the closing device 6 is closed.

Figure 4C:
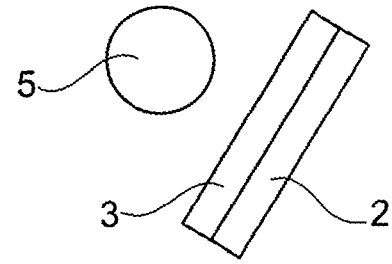
Figure 4D:
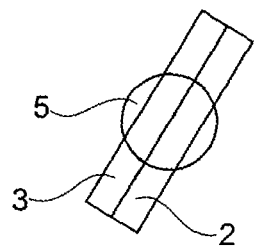
Figure 4E:
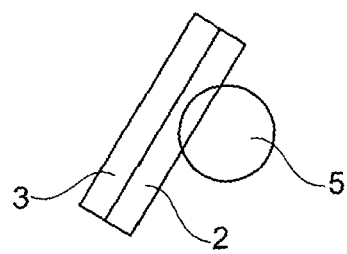

As shown in FIG. 4*c*, the incident radiation S moves further into the radiation passage region 4. The incident radiation S moves on and will exit at any point from the radiation passage region 4 and thereby, as shown in FIG. 4*d*, irradiate first the internal sensor arrangement 3 and then the external sensor arrangement 2. The incident radiation S moves on, and, as shown in FIG. 4*e*, will then no longer irradiate the internal sensor arrangement 3 but only irradiate the external sensor arrangement 2. As soon as the control device 8 recognizes this condition, the closing device 6 will be reopened. This ensures that the closing device 6 is always closed when the incident radiation S is within the radiation passage region 4.

Advantageously, a radiation passage opening 5 is planned, each with a respective closing device for the left and right eye, wherein the closing device 6 can be controlled advantageously independent of the incident radiation S.

Advantageously, the ambient radiation U is measured by the sensor 7 and the closing device 6 will only be closed and opened again if the radiation intensity of the incident radiation S, measured by the external sensor arrangement 2 at least, is higher than the intensity of the ambient radiation U or exceeds the thresholds.

Advantageously the individual sensors 2*a*, 3*a* of the external sensor arrangement 2 and preferably also on the internal sensor arrangement 3, can be measured individually or at least in groups, so that the incident radiation S can be measured, and therefrom an incident radiation direction can be calculated as it is know which of the sensors 2*a*, 3*a* were irradiated by the incident radiation S. In addition to the incident radiation direction preferably time, GPS position, height, coordinates or a radiation intensity of the incident radiation S will be measured and stored in a storage device 8*a*.

The invention claimed is:

1. A device (1) to protect the eyes from radiation, preferably in the range from 100 nm to 1 mm and in particular from UV, light, or IR, comprising of at least two sensor arrangements (2,3), an external sensor arrangement (2) and an internal sensor arrangement (3), wherein each sensor arrangement (2,3) comprises a plurality of radiation sensors (2*a*,3*a*) arranged one after another along a closed curve (2*b*,3*b*) and wherein the internal sensor arrangement (3) is surrounded by the external sensor arrangement (2), and wherein the external and internal sensor arrangement (2,3) are arranged adjacently to each other, and wherein the internal sensor arrangement (3) encloses a radiation passage region (4) and wherein the radiation passage region (4) has a radiation passage opening (S), and wherein a closing device (6) is arranged relative to the radiation passage region (4) that an incident radiation (S) passing through the radiation passage opening (5) or is at least partially attenuated, and comprised of a control device (8) connected to the internal sensor arrangement (2), the external sensor arrangement 3 and the closing device 6.

2. The device according to claim 1, characterized in that the closing device (6) has at least one mechanically movable element (6*a*) which lets the incident radiation (S) either pass or at least partially attenuate, and that the closing device (6) has a shutter speed in the range of 10-3 to 10-18 seconds.

3. The device according to claim 2, characterized in that the mechanically movable element (6*a*) is configured radiopaque and has a mirrored surface.

4. The device according to claim 2, characterized in that the mechanically movable element (6*a*) has a radiation transmission in the range of 5% to 99%.

5. The device according to claim 1, characterized in that the closing device (6) is designed as electro-optical radiation shutter.

6. The device according to one of the preceding claims, characterized in that it is designed as glasses (10) or as an spectacle attachment (10) with two reciprocally spaced-apart radiation passage regions (4) each having a radiation passage opening (5) and each a closing device (6), wherein each radiation passage region (4) is surrounded by an internal and an external sensor arrangement (2,3).

7. The device according to claim 6, characterized in that the two closing devices (6) are individually controllable.

8. The device according to claim 7, comprising of an ambient radiation sensor (7) for detecting the ambient radiation, wherein the ambient radiation sensor (7) is connected to the control device (8).

9. The device according to claim 8, comprising of a detachable optical filter (11), which can be connected in such a way with the device that the optical filter (11) is arranged in front of the sensor arrangement (2,3), the radiation passage region (4) and preferably also in front of the ambient radiation sensor (7).

10. The device according to claim 9 wherein the control device (8) comprises of a storage device (8a), in which at least the direction of incidence of the incident radiation (S) and preferably also a time stamp, GPS position, coordinates or radiation intensity of the incident radiation (S) can be stored or further communicated.

11. A method for protecting the eyes from radiation, preferably in the range from 100 nm to 1 mm and in particular from UV, light, or IR, where the eye is surrounded by at least two sensor arrangements (2,3), an external sensor arrangement (2) and an internal sensor arrangement (3), wherein each sensor arrangement (2,3) is arranged in a plurality of sequentially followed radiation sensors (2a, 3a) disposed along a closed curve path (2b, 3b), wherein the internal sensor arrangement (3) is surrounded by the external sensor arrangement (2), and wherein the internal sensor arrangement (3) encloses a radiation passage region (4), and wherein a radiation passage opening (5) is arranged in the radiation passage region (4), and wherein a closing device (6) is arranged in such a way with respect to the radiation passage opening that an incident radiation (S) will either pass or at least partially attenuate, and that the closing device (6) is closed if the external sensor arrangement (2) and subsequently the internal sensor arrangement (3) is irradiated by the incident radiation (S), and wherein the closing device (6) is re-opened if initially the internal sensor arrangement (3) and subsequently only the external sensor arrangement (2) is irradiated by the incident radiation (S).

12. The method according to claim 11, characterized in that for both, the left and for the right eye each, a radiation passage opening (5) each having a closing device (6) is planned, and that the closing devices (6) are controlled independently of the respective incident radiation (S).

13. The method according to claim 11 or 12, characterized in that an ambient radiation (U) is measured, and that the closing device (6) is only closed and re-opened if the radiation intensity of the incident radiation (S), measured by the external sensor arrangement (2) at least, is higher than the intensity of the ambient radiation (U) or if the thresholds are exceeded.

14. The method according to claim 13, characterized in that the closing device (6) can open or close with a shutter speed in the range of $10^{-3}$ to $10^{-18}$ seconds.

15. The method according to claim 14, characterized in that at least on the external sensor arrangement (2) and preferably also on the internal sensor arrangement (3) the area can be determined in which is irradiated by the incident radiation (S), and that therefrom the incident radiation direction can be calculated, and that in addition to the incident radiation direction preferably also a time stamp, GPS position, coordinates or radiation intensity of the incident radiation (S) can be stored or can be further communicated.

* * * * *